(12) United States Patent
Matvienko et al.

(10) Patent No.: US 7,388,083 B2
(45) Date of Patent: Jun. 17, 2008

(54) EPIMERIZATION OF 4'-C BOND AND MODIFICATION OF 14-CH$_3$-(CO)-FRAGMENT IN ANTHRACYCLIN ANTIBIOTICS

(75) Inventors: Victor Matvienko, Donetak (UA); Alexey Matvyeyev, Donetak (UA); Alexander F. Zabudkin, Donetak (UA); Aleksandr M. Itkin, San Diego, CA (US)

(73) Assignee: Solux Corporation, San Diego, CA (US)

( * ) Notice: Subject to any disclaimer, the term of this patent is extended or adjusted under 35 U.S.C. 154(b) by 0 days.

(21) Appl. No.: 11/367,742

(22) Filed: Mar. 4, 2006

(65) Prior Publication Data

US 2006/0223766 A1 Oct. 5, 2006

Related U.S. Application Data

(60) Provisional application No. 60/659,064, filed on Mar. 7, 2005.

(51) Int. Cl.
 C07H 15/24 (2006.01)
(52) U.S. Cl. .................................................. 536/6.4
(58) Field of Classification Search ................. 536/6.4
 See application file for complete search history.

(56) References Cited

U.S. PATENT DOCUMENTS

| | | | |
|---|---|---|---|
| 3,803,124 A | 4/1974 | Arcamone | |
| 4,112,076 A | 9/1978 | Arcamone | |
| 4,211,864 A * | 7/1980 | Vicario et al. ............... | 536/6.4 |
| 4,345,068 A | 8/1982 | Suarato et al. | |
| 4,861,870 A | 8/1989 | Oppico et al. | |
| 5,091,373 A | 2/1992 | Gatti et al. | |
| 5,874,550 A | 2/1999 | van der Rijst et al. | |
| 5,945,518 A | 8/1999 | Bigatti et al. | |
| 6,087,340 A | 7/2000 | Gatti et al. | |
| 6,376,469 B1 | 4/2002 | Shimago et al. | |
| 6,653,455 B1 | 11/2003 | Johdo et al. | |

FOREIGN PATENT DOCUMENTS

| WO | WO 86/00073 | 1/1986 |
|---|---|---|
| WO | WO 96/29335 | 9/1996 |

OTHER PUBLICATIONS

PCT International Search Report for PCT/US2006/07987, Applicant: Solux Corporation, Form PCT/ISA/210 and 220, dated Jul. 28, 2006 (3 pages).
PCT Written Opinion for PCT/US2006/07987, Applicant: Solux Corporation, Form PCT/ISA/237, dated Jul. 28, 2006 (4 pages).
Office Action dated Jun. 13, 2006, for related U.S. Appl. No. 10/877,221, filed Jun. 25, 2004, Inventor: Victor Matvienko (7 pages).
Response to Office Action dated Jun. 13, 2006, mailed Sep. 13, 2006, for related U.S. Appl. No. 10/877,221, filed Jun. 25, 2004, Inventor: Victor Matvienko (9 pages).
Office Action dated Oct. 24, 2006, for related U.S. Appl. No. 10/877,221, filed Jun. 25, 2004, Inventor: Victor Matvienko (7 pages).
Reponse to Office Action dated Oct. 24, 2006, mailed Jan. 23, 2007, for related U.S. Appl. No. 10/877,221, filed Jun. 25, 2004, Inventor: Victor Matvienko (9 pages).
Office Action dated Mar. 16, 2007, for related U.S. Appl. No. 10/877,221, filed Jun. 25, 2004, Inventor: Victor Matvienko (6 pages).
Request for Continued Examination mailed Sep. 17, 2007, for related U.S. Appl. No. 10/877,221, filed Jun. 25, 2004, Inventor: Victor Matvienko (1 pages).
Response to Office Action dated Mar. 16, 2007, mailed Sep. 17, 2007, for related U.S. Appl. No. 10/877,221, filed Jun. 25, 2004, Inventor: Victor Matvienko (10 pages).
Declaration of Philipp Alexander Titulski under 37 C.F.R. § 1.132, mailed Sep. 17, 2007, for related U.S. Appl. No. 10/877,221, filed Jun. 25, 2004, Inventor: Victor Matvienko (3 pages).
Declaration of Anil Dhedia under 37 C.F.R. § 1.132, mailed Sep. 17, 2007, for related U.S. Appl. No. 10/877,221, filed Jun. 25, 2004, Inventor: Victor Matvienko (2 pages).
Declaration of Dr. Waldemar Priebe under 37 C.F.R. § 1.132 with attached curriculum vitae, mailed Sep. 17, 2007, for related U.S. Appl. No. 10/877,221, filed Jun. 25, 2004, Inventor: Victor Matvienko (38 pages).
Office Action dated Nov. 6, 2007, for related U.S. Appl. No. 10/877,221, filed Jun. 25, 2004, Inventor: Victor Matvienko (6 pages).
Interview Summary dated Dec. 11, 2007, for related U.S. Appl. No. 10/877,221, filed Jun. 25, 2004, Inventor: Victor Matvienko (4 pages).

(Continued)

*Primary Examiner*—Elli Peselev
(74) *Attorney, Agent, or Firm*—Vista IP Law Group LLP

(57) ABSTRACT

A method of synthesizing R1, R2-substituted-4' (ax. or eq.)-OH anthracyclines and their corresponding salts of Formula (1) from daunorubicin or N-Trifluoroacetyl-4-R1-derivatives of daunorubicin, wherein R1 is defined as H, OH, and 4'-HO is defined as ax[ial]. The method includes producing N-Trifluoroacetyl daunorubicin and treating the N-Trifluoroacetyldaunorubicin or N-Trifluoroacetyl-4-R$_1$-derivatives of daunorubicin, wherein R$_1$ is defined as H, OH, with dimethylsulfoxide activated by different acylating agents. The attained intermediate product is then treated with a strong base (ex. tertiary amines) resulting in the 4'-keto-N-Trifluoroacetyl-4-R$_1$ daunorubicin wherein R$_1$ is defined as H, OH, OMe. The 4'-keto-N-Trifluoroacetyl-4-R$_1$-daunorubicin is reacted with a reducing agent, a derivative of a borohydride of an alkaline metal MHBL$_3$, to produce N-Trifluoroacetyl-4'-epi-4-R$_1$-daunorubicin. The N-Trifluoroacetyl-4'-epi-4-R$_1$-daunorubicin undergoes hydrolysis in a basic solution to produce a derivate of an anthoacyclin which is halogenized [by complex halogenides] to form a 14-Hal-derivative. This result is then hydrolyzed by well-known methods in the presence of a formate of an alkaline metal to form the desired final compound.

3 Claims, No Drawings

OTHER PUBLICATIONS

PCT International Search Report for PCTUS2004/20679, Applicant: Solux Corporation, Form PCT/ISA/220 and 210, dated May 4, 2006 (5 pages).

PCT Written Opinion of the International Searching Authority for PCT/US2004/20679, Applicant: Solux Corporation, Form PCT/ISA/237, dated May 4, 2006 (4 pages).

Trimethylsilyl Trifluoromethanesulfonate as an Excelent Glucosidation Reagent for Antracycline Synthesis. Simple and Efficient Synthesis of Optically Pure 4-Demethoxydaunorubicin. Y. Kimura, M. Suzuki, T. Matsumoto, R. Abe, Sh. Terashima. Chem. Letters, 1984, pp. 501-504.

* cited by examiner

EPIMERIZATION OF 4'-C BOND AND MODIFICATION OF 14-CH₃-(CO)-FRAGMENT IN ANTHRACYCLIN ANTIBIOTICS

RELATED APPLICATIONS

This Application claims priority to U.S. provisional Application No. 60/659,064, filed Mar. 7, 2005. U.S. provisional Application No. 60/659,064 is incorporated by reference as if set forth fully herein.

FIELD OF THE INVENTION

The field of the invention generally relates to chemical methods used to produce anthracyclines. More specifically, the field of the invention relates to methods and processes utilized in production of anthracyclins of Formula (1) ($R_1$=H, OH, OMe; $R_2$=H, OH, 4'-HO eq[uatorial] or ax[ial]), $An^-$ - - - anion of any strong acid (as an example, in a particular case of 4'-epirubicin, $An^-$ is described as $Cl^-$).

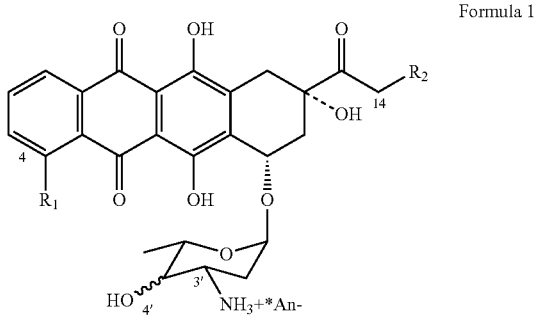

Formula 1

BACKGROUND OF THE INVENTION

Anthracyclines form one of the largest families of naturally occurring bioactive compounds. Several members of this family have shown to be clinically effective antineoplastic agents. These include, for example, daunorubicin, doxorubicin, idarubicin, epirubicin, pirarubicin, zorubicin, aclarubicin, and carminomycin. For instance, these compounds have been shown to be useful in bone marrow transplantation, stem cell transplantation, treatment of breast carcinoma, acute lymphocytic and non-lymphocytic leukemia, chronic lymphocytic leukemia, non-Hodgkin's lymphoma, and other solid neoplasias.

The most common starting material, utilized for synthesis of semi-synthetic derivatives of anthracyclins, is Daunorubicin. In Daunorubicin, the 4'-hydroxyl group of aminoglycoside fragment is in axial configuration. For production of epi-derivatives, it is necessary to change the configuration of this hydroxyl group from axial to equatorial. This can be attained in two ways: oxidation of the 4'-OH group to ketone (with loss of an optical center) with further stereospecific reduction to the required equatorial configuration [1]; or biomolecular nucleophilic substitution of 4'-OTf—derivative, accompanied by Walden inversion and, hence, by epimerization [2]. These modifications can be accomplished both on intact anthracyclin molecules and on isolated aminosugars, derived as a result of algycone removal [3] or separately synthesized [4]. Simplicity of working with isolated aminosugar is countered by difficulty of a stereospecific reaction of aglycone glycosilation. In this situation, more times than not, the real yield of the required α-anomer of anthracyclin appears to be less than those previously declared [3,4,5].

Modification of 14-$R_2$=H to 14-$R_2$=OH is conducted by halogenization of the end methyl group with molecular bromine or iodine at room or lower (6-10° C.) temperature in a mixture of anhydrous methanol and dioxane [6]. Earlier patents described bromination of the unprotected ketone group; afterwards, ketone protection the 13-C=O group was demonstrated [7]. Next, the halogen undergoes nucleophilic substitution with hydroxyl or a carboxylate anion with creation of an intermediate ester 14-$R_2$=OCOAlk (Ar), where, most commonly, $R_2$=OCOH. This ester is then hydrolyzed to 14-$R_2$=OH.

The described methods, especially those that require glycosilation stage, require utilization of a significant number of protection groups in order to provide an adequate modification of anthracyclin molecule. Placement and removal of protection groups significantly increases the number of synthetic stages, and decreases the yield of the product. The subject of the present patent is decrease in the number of stages of the synthetic process and increase in the selectivity of the chemical reactions, including stereospecificity, during synthesis both currently-known and future novel anthracyclins.

SUMMARY OF THE INVENTION

The present invention relates to processes used to prepare R1, R2-substituted-4' (ax. or eq.)-OH anthracyclines and their corresponding salts of Formula (1) from daunorubicin or N-Trifluoroacetyl-4-R1-derivatives of daunorubicin, wherein R1 is defined as H, OH, and 4'-HO is defined as ax[ial]. The steps involved in this novel process are:

(1) producing N-Trifluoroacetyl daunorubicin of Formula (2) (R1=OMe)

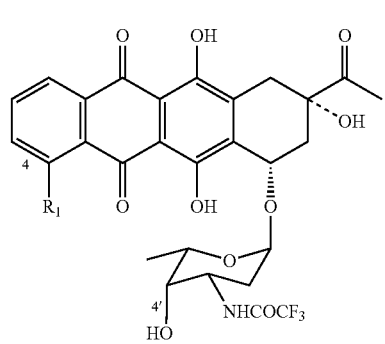

Formula 2

(2) treating the N-Trifluoroacetyldaunorubicin or N-Trifluoroacetyl-4-$R_1$-derivatives of daunorubicin of Formula (2), wherein $R_1$ is defined as H, OH, with dimethylsulfoxide activated by different acylating agents (AcX)

AcX=Py $SO_3$, $SOCl_2$, $PHal_3$, $POHal_3$; Hal=Cl, Br;
Ac=AlkCO; OC—$(CH_2)_n$—CO, n=0 to 4; $AlkSO_2$; ArCO; Ar $SO_2$,
Alk=alkyl of halogenalkyl radical
Ar=phenyl or substituted phenyl radical
X=Cl, Br, I, OAc.

The attained intermediate product is then treated with a strong base (ex. tertiary amines) resulting in the 4'-keto-N-Trifluoroacetyl-4-$R_1$ daunorubicin of Formula (3):

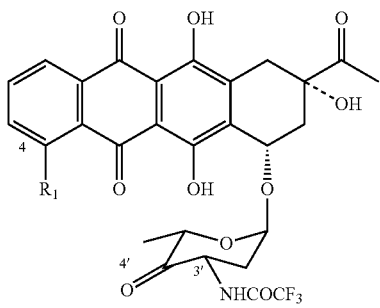

Formula 3 wherein $R_1$ is defined as H, OH, OMe.

(3) reacting the 4'-keto-N-Trifluoroacetyl-4-$R_1$-daunorubicin of Formula (3) with a reducing agent, a derivative of a borohydride of an alkaline metal $MHBL_3$, where M=Li, Na, K; L=AlkO, AlkCOO, ArCOO (Alk=Methyl ("Me"), Ethyl ("Et"), n-Propyl ("n-Pr"), Allyl ("All"); Aryl ("Ar")=Phenyl ("Ph") or subst. Ph=Ph-Alk. to produce N-Trifluoroacetyl-4'-epi-4-$R_1$-daunorubicin, Formula (4), wherein $R_1$ is defined as H, OH, OMe. Alk=Alkyl Phenyl radical is substituted at ortho-, meta-, Ph-Alk=

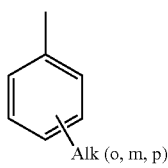

or para-positions with alkyl groups mentioned above.

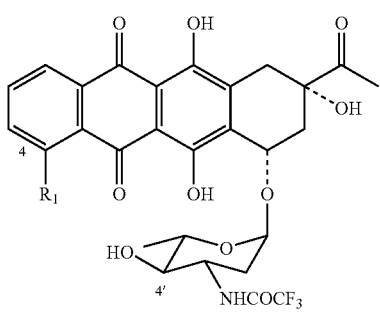

Formula 4

(4) hydrolyzing N-Trifluoroacetyl-4'-epi-4-$R_1$-daunorubicin in a basic solution to produce a derivate of Formula (5), wherein $R_1$ is defined as H, OH, OMe; 4'-HO is eq[uatorial]

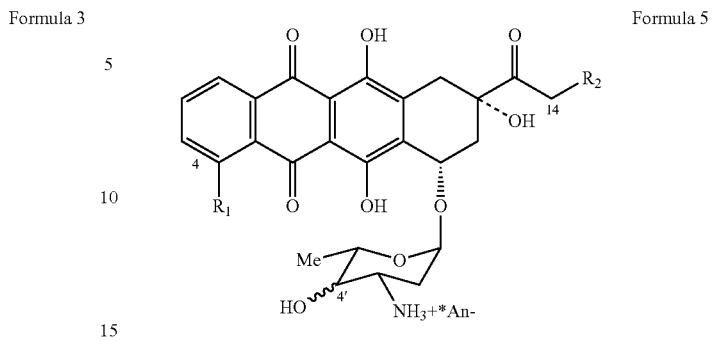

Formula 5

(5) halogenization of anthracyclins of Formula (5) (where $R_1$ is defined as H, OH, OMe; $R_2$ is defined as H; 4'-OH is ax[ial] or eq[atorial]; An⁻ is an anion of a strong acid) at C14 position is accomplished by reaction with complex halogenides described by Formula

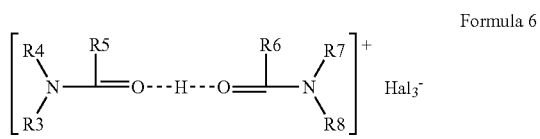

Formula 6 where $R_3$ through $R_8$ are defined as H or a hydrocarbon radical of 1 to 4 carbon chains ($C_1$-$C_4$); Hal is Cl, Br, I.

The attained 14-Hal-derivative, Formula (7), ($R_1$ is defined as H, OH, OMe; 4'-HO is ax[ial] or eq[uatorial]; Hal is Cl, Br, I; An⁻ is an anion of a strong acid) is hydrolyzed by well-known methods in the presence of a formate of an alkaline metal with a final result of a product of Formula (1)

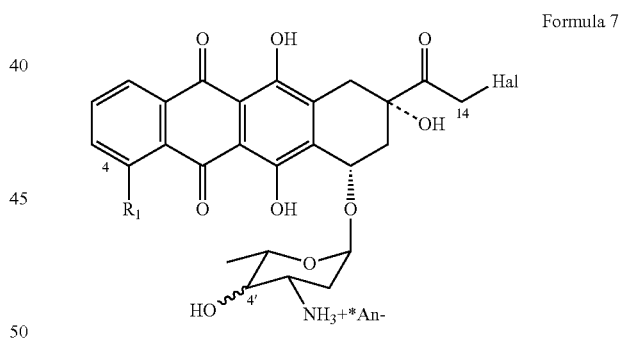

Formula 7

The present invention therefore provides a novel method of synthesis of anthracyclin derivatives with utilization of innovative reagents and processes which are distinct as to stages of placement of protective groups, oxidation, reduction, and halogenization. The novel method allows: (a) a decrease in the number of synthetic stages; (b) a decrease in the number of impurities; (c) simplification of extraction and purification; and an increase in the total yield of the target product.

DETAILED DESCRIPTION OF THE INVENTION

The method of preparing R1, R2-substituted-4' (ax. or eq.)-OH anthracyclines and their corresponding salts of Formula (1) from daunorubicin or N-Trifluoroacetyl-4-R1-derivatives of daunorubicin, wherein R1 is defined as H, OH, and 4'-HO is defined as ax[ial], according to the present invention comprises the following steps.

I. Synthesis of N-trifluoroacetate Anthracyclin Derivatives of Formula (2)

N-TFA antrhacylcin derivative of Formula (2) (where $R_1$ is defined as H, OH, OMe; $R_2$=H) is synthesized by acylation of a corresponding anthracyclin (most commonly daunorubicin) with trifluoroacetic acid in anhydrous, aprotic and immisable-in-water solvents, preferably dichloromethane, followed by a soft hydrolysis of the resultant amidoester in a biphasic system of aqueous base—organic solvent, pH 8-10 (FIG. 1).

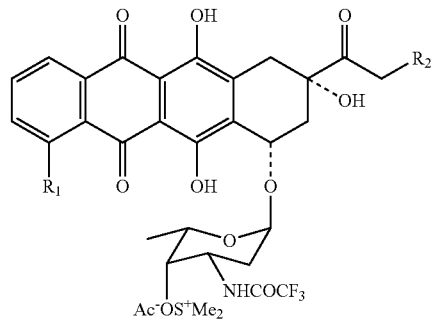

Formula 8

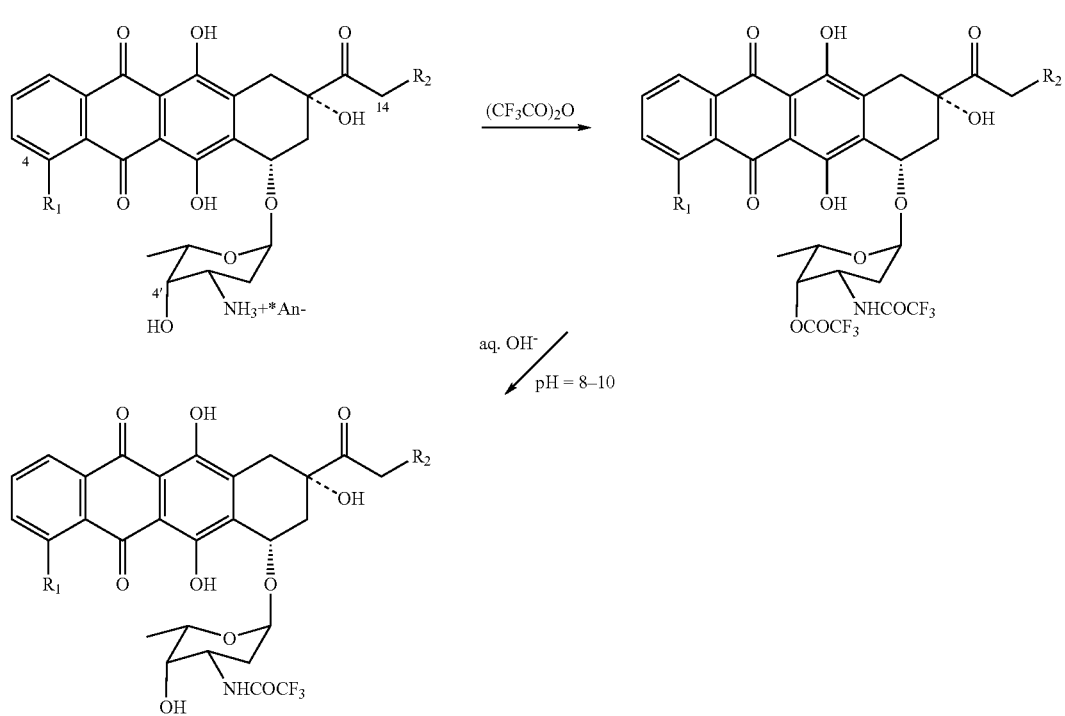

Figure 1

II. Synthesis of a 4'-keto-N-trifluoroacetyl Anthracyclin Derivatives

4'-keto-N-TFA anthracyclin derivatives are attained by reaction between N-TFA antrhacylin derivatives of Formula (2) ($R_1$ is defined as H, OH, OMe; $R_2$=H) with dimethylsylfoxide that was activated by various acylating agents (AcX) at temperatures of −80° C. to 0° C., preferably −60±5° C. This results in a formation of a sulfoxy salt (Formula (8)), which splits under the action of a strongly basic tertiary amines to form 4'-keto-N-TFA antrhacyclin derivatives ($R_2$=H).

In optimal conditions, the yield of a target ketone can be ≧90% (HPLC) (FIG. 2).

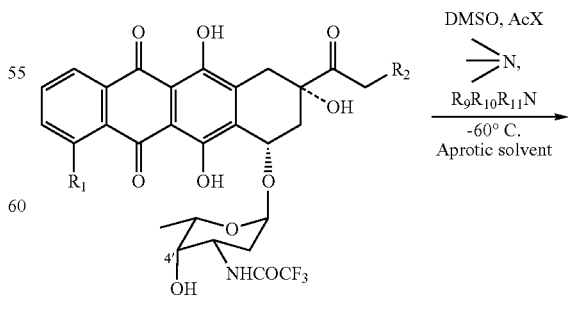

FIG. 2

4'-axial

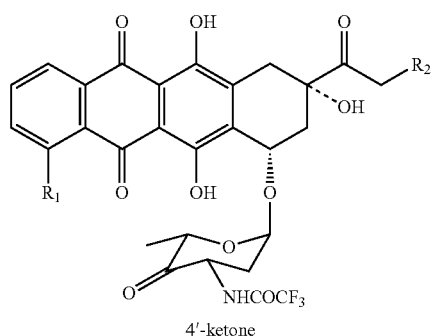

4'-ketone where AcX, Ac, X are as defined earlier $R_9$, $R_{10}$, $R_{11}$=alkyl [$C_nH_{2n+2}$ n=1-8] or cycloalkyl [$C_nH_{2n}$ n=4-7]

$R_{10}$, $R_{11}$=—(CH$_2$)$_n$— where n=3 to 6.

N=cyclic or polycyclic tertiary strongly basic amine, ex. 1,8-diazabicyclo(5.4.0)undec-7-e-ne ("DBU"), quinuclidine Aprotic Solvent=such aprotic solvents as dimethylsulfoxide ("DMSO"), n,n-Dimethylacetoacetamide ("DMAA"), hexamethylphosphoramide ("HMPA"), dichloromethane ("DCM") etc., as well as halogenalkanes, aromatic hydrocarbons and mixtures thereof.

III. Synthesis of 4'-epi-N-Trifluoroacetyl Derivatives of Anthracyclins

4'-epi-N-trifluoroacetyl derivatives of anthracyclins, Formula (4), ($R_1$ is defined as H, OH or OMe; $R_2$=H) are produced by way of stereospecific reduction of 4'-keto-N-TFA-anthracyclins with derivatives of borohydride of alkaline metals: MHBL$_3$, FIG. (3):

Figure 3

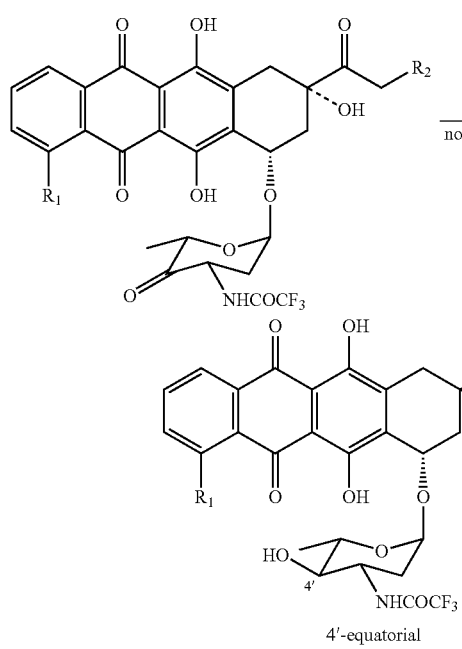

4'-equatorial where M and L are as defined earlier.

Reaction is conducted in non-reducible solvents: alcohols, ethers, hydrocarbons and halogenized hydrocarbons and their mixtures, but most commonly in tetrahydrofurane. Reaction temperature ranges from −35° C. to 30° C., preferably at 20±5° C.

IV. Synthesis of 4'-epi-derivatives of anthracyclins

Removal of the N-TFA protection group from 4'-epi-N-TFA derivatives of antrhacyclins ($R_1$ is defined as H, OH or OMe; $R_2$=H) is attained by treatment with aqueous base, pH=10-13, temperature from 0° C. to 40° C., preferably 20±5° C. [1].

V. Modification of 14-CH3 Radical to 14-CH20H in an Aglycone Fragment of Antrhacyclin Antibiotics In the claimed novel method, halogenization of anthracyclin derivatives ($R_1$ is defined as H, OH or OMe; $R_2$=H; 4'-HO eq[uatorial] or ax[ial]. FIG. (4)) is accomplished by utilization of complex halogenides, Formula (6), as halogenizing agents. This approach permits to decrease the number of synthesis stages, and to increase the yield and purity of the final product.

Figure 4

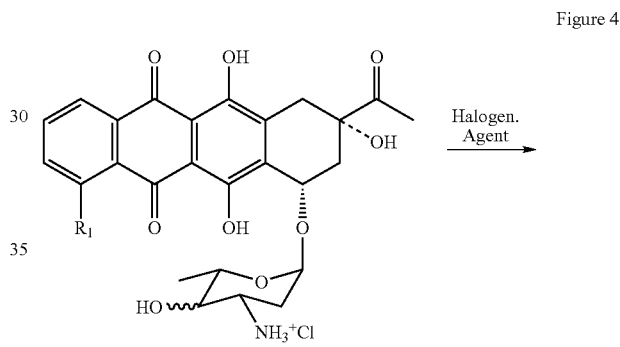

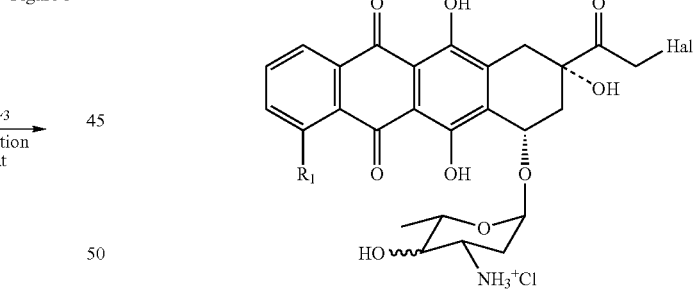

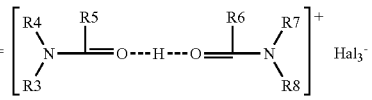

Solvents utilized in this reaction are amides, simple ethers and mixtures thereof; preferably dimethylformamide and tetrahydrofuran.

Reaction is conducted at temperature of 20-60° C. for 2-20 hours; preferably at 50° C. for 3 hours. Attained 14-halogen derivative is hydrolyzed in aqueous acetone solution in the presence of salts of carboxylic acids, preferably sodium formate, pH=2.5-5.5.

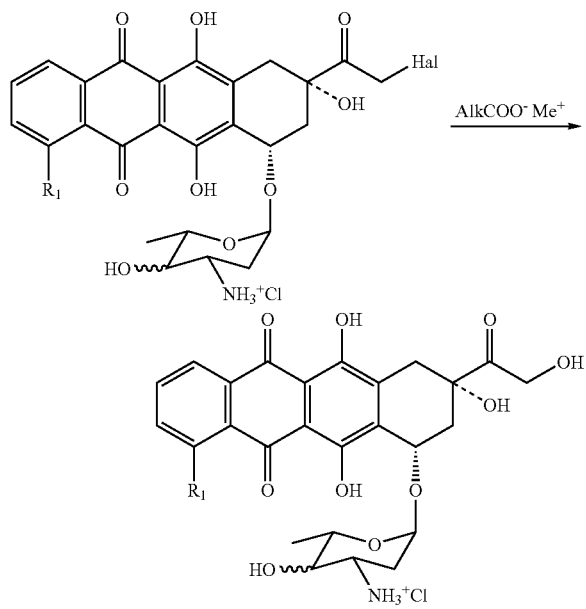

Figure 5

EXAMPLE 1

(a) 5 grams of daunorubicin ($R_1$=OMe, $R_2$=H) is suspended in 200 ml of dichloromethane (DCM) and chilled to 0° C. While intensely stirring the suspension, drops of trifluoroacetic anhydride in DCM (7 ml: 15 ml) are slowly added over a period of 1 hour.

(b) Resulted mixture is kept at 0° C. for another 0.5 hours and then pored in 250 ml of distilled water and mixed with further separation of the organic layer.

(c) 200 ml of saturated solution of sodium bicarbonate is added to the resulted organic layer, and the mixture is left at room temperature, being intensely stirred, for 15-24 hours, in order to undergo hydrolysis 3'-N,4'-O-di-trifluoro-acetyldaunomycin.

(d) After completion of hydrolysis (controlled according to HPLC), the organic layer is separated and subjected to evaporation under reduced pressure conditions until fully dry.

(e) After evaporation, 5 grams of N-trifluoroacetyldaunorubicin is produced with a purity 93% (Confirmed by HPLC).

(f) The N-trifluoroacetyldaunorubicin from step (e) of Example 1 is utilized in the next synthetic step in Example 2 without additional purification.

EXAMPLE 2

(a) 5 ml of DMSO is dissolved in 100 ml of DCM and chilled down to −60° C. while being stirred. After that, 1 ml of oxalylchloride in 5 ml of DCM is added to the solution, which is then incubated at −60° C. for 40 minutes.

(b) 5 gram of N-trifluoroacetyldaunorubicin is dissolved in 50 ml of DCM and add to the reaction mixture over a 20-minute period, while maintaining the temperature in a −60±5° C. range. The reaction mixture is then incubated for 1 hour.

(c) 7 ml of triethylamine is added to the reaction mixture at a temperature ≦−60° C. Total time of contact between the reaction mixture and triethylamine is 10 minutes.

(d) A solution of 5 ml of acetic acid in 10 ml of DCM is added to the reaction mixture and stirred for 2 minutes.

(e) Reaction mixture is then pored in a 300 ml of distilled water, stir and separate an organic layer. This step is repeated 3 times.

(f) Organic layer is evaporated in rotary evaporator under reduced pressure conditions.

(g) After evaporation, 4.7 gram of 4'keto-N-trifluoro-acetyldaunorubicin is produced with a purity 89% (Confirmed by HPLC).

(h) The 4'keto-N-trifluoroacetyldaunorubicin from step (g) of Example 2 is utilized in the next synthetic step in Example 3 without additional purification.

EXAMPLE 3

(a) 4.7 grams of 4'keto-N-trifluoroacetyldaunorubicin is dissolved in 180 ml of tetrahydrofuran and, while stirring, 2.1 grams of sodium triacetylborohydride is added over a 40-minut period. While being agitated, the reaction mixture is incubated for 1 hour at a temperature range of 20±2° C.

(b) Reaction mass is then transfered into a mixture of 150 ml of DCM +300 ml of distilled water +2 ml of 1M hydrochloric acid, and stirred. Organic layer is separated and then washed twice with 300 ml aliquots of distilled water.

(c) After evaporation, 4.6 g of 4'epi-N-trifluoro-acetyldaunorubicin is produced with a purity 79% (Confirmed by HPLC).

(d) Produced crude product then undergoes purification in preparative chromatograph. After evaporation of the eluate, 3.0 gram of 4'epi-N-trifluoroacetyldaunorubicin is produced with a purity 95% (Confirmed by HPLC).

EXAMPLE 4

3.0 gram of 4'epi-N-trifluoroacetyldaunorubicin is suspended in 200 ml of distilled water at temperature 30° C., and 10 ml of 1.0N NaOH solution is then added. The mixture is incubated for 30 minutes, and then neutralized to pH 7 with a solution of hydrochloric acid and sent to preparative chromatography. After evaporation of eluate, 2.1 g of 4'epi-daunorubicin is produced with a purity 96% (Confirmed by HPLC).

EXAMPLE 5

(a) 2.1 gram of epidaunomycin hydrochloride is dissolved in 70 ml of dimethylformamide, and 2.8 gram of hydrogen dibromobromate bis (dimethylformamide) is added to the mixture. The mixture is then incubated at 40° C. for 2 hours.

(b) Reaction mixture is pored in 350 ml of acetonitrile. Precipitated sediment is filtered and washed with acetonitrile; the solvent is removed.

(c) Solid sediment is dissolved in a mixture of 80 ml of acetone +80 ml of 0.25 M aqueous solution of hydrogen bromide +8 grams of sodium formate. The reaction mixture is incubated for 30 hours at 35° C.

(d) Reaction mixture undergoes preparative chromatography where epirubicin-containing fraction is separated.

(e) Eluate is evaporated, and the residue is crystallized by adding acetone.

(f) The yield of this process is 1.3 g of epirubucine hydrochloride of 99,8% purity (Confirmed by HPLC).

We claim:

1. A method of producing 4'-keto-N-Trifluoroacetyl-4-$R_1$ daunorubicin having a formula represented by Formula (3), wherein $R_1$ is H, OH, or OMe, comprising:

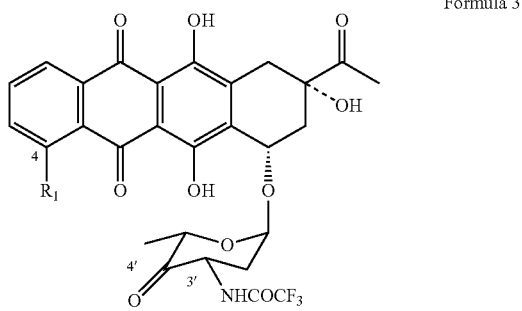
Formula 3

(a) reacting N-Trifluoroacetyl daunorubicin having a formula represented by Formula (2), wherein $R_1$ is H, OH or OMe, with AcX activated DMSO in aprotic solvent,

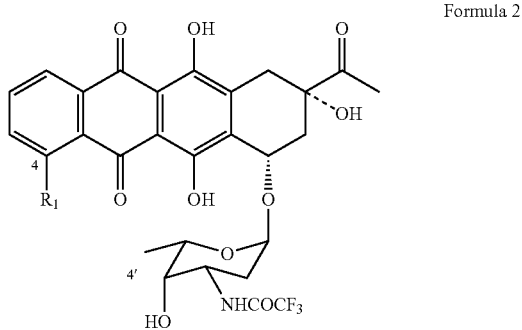
Formula 2 wherein
AcX=$PySO_3$, $SOCl_2$, $PHal_3$, $POHal_3$; Hal=Cl, Br
Ac=AlkCO; OC—$(CH_2)_n$—CO, n=0÷4; $AlkSO_2$; ArCO; $ArSO_2$
Alk=alkyl of halogenalkyl radical,
Ar=phenyl or substituted phenyl radical,
X=Cl, Br, I, OAc; and
Aprotic Solvent=DMSO, DMAA, HMPA, Acetonitrile, DCM and other halogenalkanes, aromatic hydrocarbons and mixtures thereof,
to produce an intermediate sulfoxy salt represented by Formula (8),

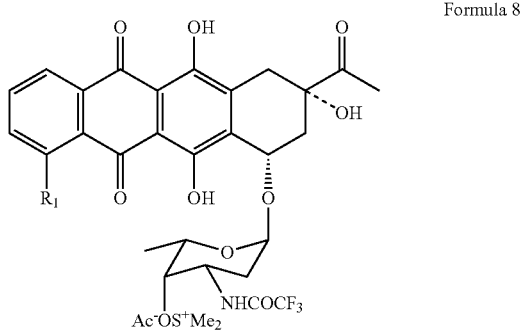
Formula 8

(b) reacting the intermediate sulfoxy salt represented by Formula (8) with a strong base tertiary amine to produce the 4'-keto-N-Trifluoroacetyl-4-$R_1$ daunorubicin of Formula (3), wherein said strong bases utilized for decomposition of the intermediate, Formula (8), are tertiary amines represented by the formula $NR_9R_{10}R_{11}$, wherein $R_9$, $R_{10}$, $R_{11}$=alkyl [$C_nH_{2n+2}$ n=1-8] or cycloalkyl [$C_nH_{2n}$ n=4-7]; and $R_{10}$, $R_{11}$=—$(CH_2)_n$— n =3-6.

2. A method of producing N-Trifluoroacetyl-4'-epi-4-$R_1$-daunorubicin having a formula represented by Formula (4), wherein $R_1$ is defined as H, OH, OMe, comprising:

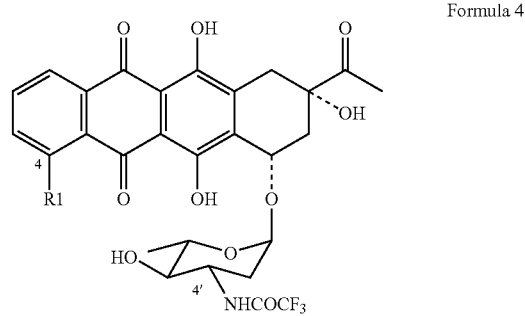
Formula 4

(a) reacting 4'-keto-N-Trifluoroacetyl-4-$R_1$ daunorubicin having a formula represented by Formula (3) with complex hydrides of formula $MHBL_3$ as a stereospecific reducing agent, wherein M=alkaline metal Li, Na, K; L=AlkO, AlkCOO (Alk=Me, Et, n-Pr, All), to produce N-Trifluoroacetyl-4'-epi-4-$R_1$-daunorubicin having a formula represented by Formula (4),

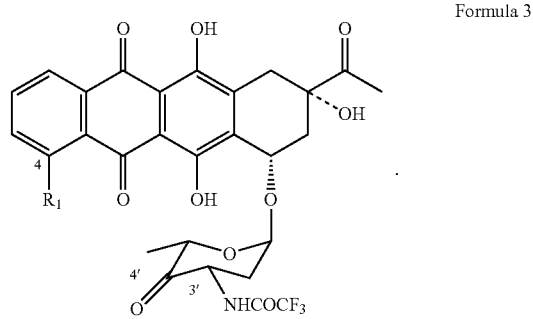
Formula 3

3. A method of producing an anthracyclin having a formula represented by Formula (1), wherein $R_2$=Hal, comprising:

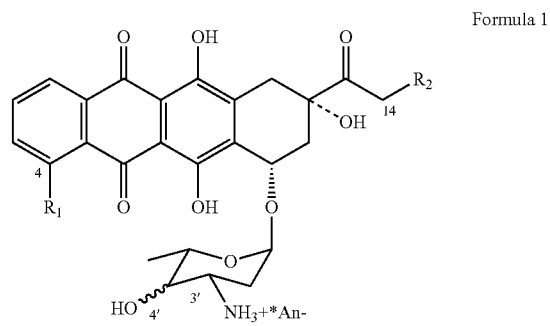
Formula 1

(a) reacting an anthracyclin having a formula represented by Formula (5), wherein $R_1$ is defined as H, OH, OMe; 4'—OH is ax[ial] or eq[atorial]; $An^-$ is an anion of a strong acid

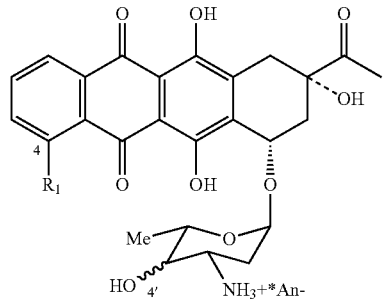

Formula 5 with complex halogenides having a formula represented by Formula (6), wherein $R_3$-$R_8$=H or a hydrocarbon radical $C_1$-$C_4$, Hal =Cl, Br or I, as a halogenizing agent, and the solvent utilized for the halogenization process is an aprotic solvent comprising amides, simple ethers and their mixtures,

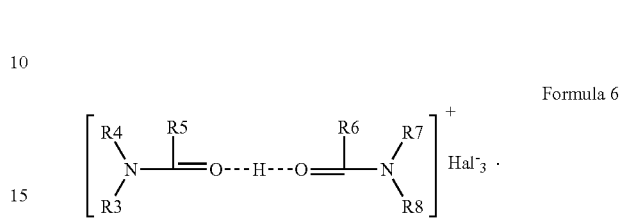

Formula 6

* * * * *